United States Patent [19]

Porowski et al.

[11] Patent Number: 4,817,441
[45] Date of Patent: Apr. 4, 1989

[54] PROCESS AND APPARATUS FOR OBTAINING A GAS SAMPLE

[75] Inventors: Jan S. Porowski; Manu L. Badlani, both of Pittsburgh; Edward J. Hampton, Murrysville; William J. O'Donnell, Bethel Park, all of Pa.

[73] Assignee: O'Donnell & Associates, Inc., Pittsburgh, Pa.

[21] Appl. No.: 188,914

[22] Filed: May 2, 1988

[51] Int. Cl.$^4$ .................................................. G01N 1/00
[52] U.S. Cl. ........................... 73/863.12; 73/863.23; 73/863.81; 55/97; 55/270; 241/19; 241/24; 241/101.3
[58] Field of Search ............... 55/270, 97; 241/31, 241/101.3, 19, 24; 73/863.11, 863.23, 863.81, 864.21, 866.5, 864.73, 863.12

[56] References Cited

U.S. PATENT DOCUMENTS

| | | | |
|---|---|---|---|
| 2,519,303 | 8/1950 | Whitehouse | 73/863.11 |
| 4,379,412 | 4/1983 | Wood | 73/864.73 |
| 4,484,481 | 11/1984 | Laird et al. | 73/863.12 |
| 4,653,698 | 3/1987 | Cooper et al. | 241/31 |

FOREIGN PATENT DOCUMENTS

| | | | |
|---|---|---|---|
| 2308649 | 10/1973 | Fed. Rep. of Germany | 73/863.11 |
| 67732 | 11/1979 | Japan | 73/864.73 |

*Primary Examiner*—Bernard Nozick
*Attorney, Agent, or Firm*—Joseph J. Carducci

[57] ABSTRACT

A process for obtaining a gaseous sample from a stream containing solid particulate material, a gas, water and steam which comprises withdrawing a stream containing said particulate material, a gas, water and steam from a system containing the same through an elongated tubular member extending into said system and discharging said stream from said tubular member externally of said system, heating said stream in its passage through said tubular member, removing from said tubular member externally of said system a gaseous sample consisting essentially of said gas and said steam through a porous section of said elongated tubular member having openings in the wall thereof smaller in cross-section than the solid particulate material in said stream, and apparatus for carrying out the same.

11 Claims, 2 Drawing Sheets

PROCESS AND APPARATUS FOR OBTAINING A GAS SAMPLE

BACKGROUND OF THE INVENTION

1. Field of the Invention

This invention relates to a novel process for obtaining an accurate, or representative, sample of gas from a system containing solid particulate material, a gas, water and steam and a novel apparatus therefor.

2. Description of Prior Art

When coal is to be burned in a furnace, it is first passed through a pulverizer to obtain coal particles of a size suitable for burning in the furnace. From about 15 to about 20 percent of the air required for combustion in the furnace is also introduced into the pulverizer to transport the coal particles thereto. In some cases, the air introduced into the pulverizer also helps to dry the coal therein. Since coal contains some water, water will also be present in the pulverizer system.

Because of the relatively high oxygen content in the pulverizer and the tendency of coal particles to agglomerate therein, there is a potential for an explosion therein. When such danger arises, the system in the pulverizer can be rendered inert by the introduction therein of sufficient steam to reduce the oxygen content to about nine volume percent, or less, within about two to about four minutes. In order to make sure that the oxygen content of the mixture in the pulverizer is below the desired amounts, it is necessary to obtain accurate and rapid measurements, of the contents of the pulverizer, particularly the oxygen content.

Unfortunately, instrumentation presently installed in commercial coal pulverizers for measuring the oxygen content in such pulverizers does not provide reliable readings therein after the introduction of steam. During the inerting procedure, the walls of the pulverizers and the instrument tubing therein remain at temperatures significantly lower (about 120° F.) than the saturation temperature of the air-steam mixture flowing through the central, or main, portion of the pulverizer. Consequently, due to the resulting condensation of some of the steam, the partial pressure of the steam in the sample reaching the oxygen analyzer cell is significantly lower than that existing in the pulverizer for the steam (about 50 volume percent) and therefore results in an inaccurate reading therefor. In addition, the resulting condensate causes sedimentation of the local particles, resulting in reduction of flow of the air-steam stream to the oxygen analyzer cell, further degrading the sampling operation.

SUMMARY OF THE INVENTION

We have found that we can prevent, or substantially inhibit, condensation of steam in the air-steam sample and thereby obtain an accurate reading of the oxygen contact in the coal pulverizer by withdrawing a stream containing coal particles, air, water and steam from the interior of said coal pulverizer through an elongated tubular member extending into said coal pulverizer and discharging said stream from said tubular member externally of said coal pulverizer, heating said stream in its passage through said tubular member, removing from said tubular member externally of said coal pulverizer a gaseous sample consisting essentially of air and steam through a porous section of said elongated tubular member having openings in the wall thereof smaller in cross-section than said coal particles in said stream. The apparatus for carrying out the above process is also novel and is also claimed herein.

BRIEF DESCRIPTION OF THE INVENTION

Figure 1:
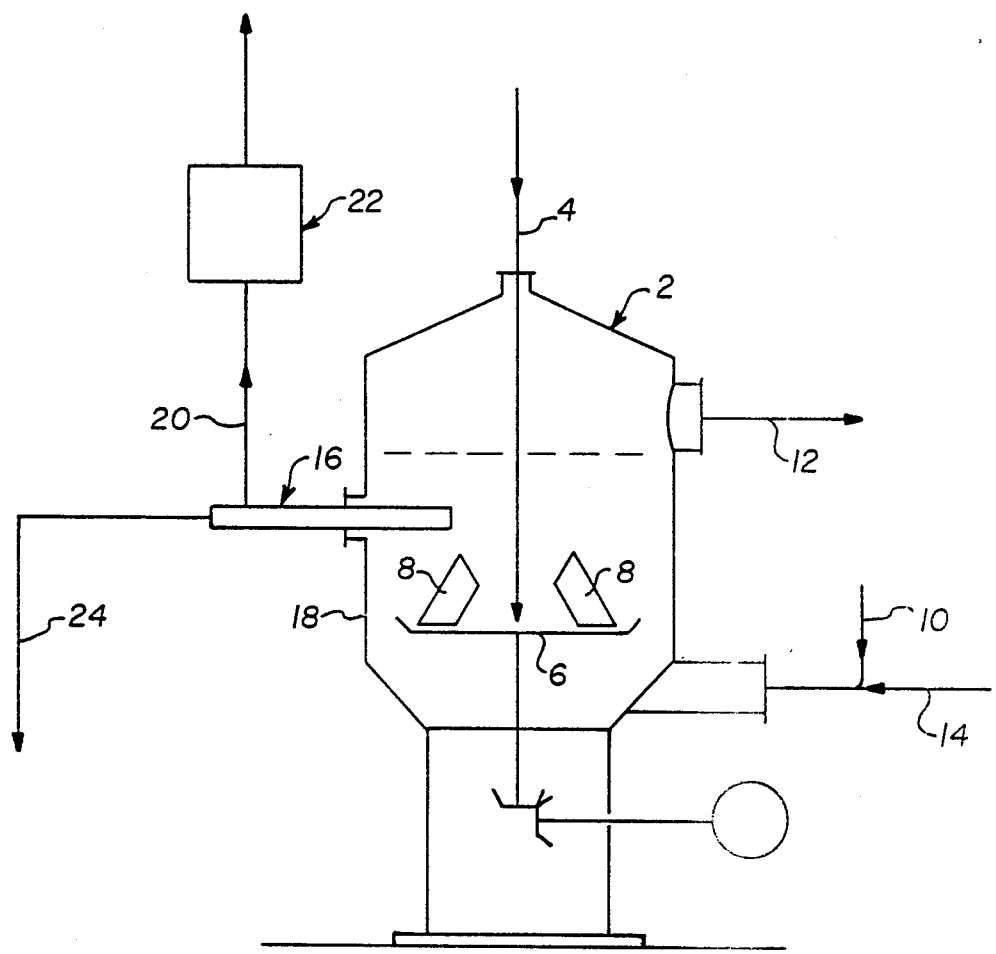
FIG. 1 is a schematic representation of the environment in which our novel claimed apparatus is used to carry out the novel process claimed herein.

Referring to FIG. 1, reference numeral 2 designates a coal pulverizer in which coal is introduced therein by line 4, falls on a rotating bowl 6, and is pulverized thereon by rollers 8. Air is also introduced into coal pulverizer 2 by line 10, picks up pulverized coal therein and transports it by way of exit line 12 to the furnace, not shown, wherein the pulverized coal is mixed with additional air and burned. The oxygen content of the system is normally about 15 to about 21 volume percent.

When danger arises, and an explosion may be possible, the air flow in line 10 is substantially reduced, or cut off, and steam is introduced into the pulverizer 2 by line 14 in order to inert the system and thereby reduce the possibility of an explosion. The amount of steam introduced into coal pulverizer 2 to effect this desired result must be at least sufficient to reduce the oxygen content therein to a level of about nine volume percent, or even less. When this situation occurs, the volume percent of the steam in the coal pulverizer can be in the range of about 30 to about 100 volume percent, the volume percent of air in the range of about 0 to about 70 volume percent, the weight percent of water about 20 to about 90, the temperature in the range of about 125° to about 275° F. and the pressure in the range of about −7 to about +3 inches of water column. The coal particles will have a mean average diameter of about 5 to about 500 microns.

The claimed device herein for analyzing the oxygen content of the mixture is coal pulverizer 2 is a probe 16 that extends through the wall 18 of the coal pulverizer 2 into the interior thereof. A sample of the contents in pulverizer 2 is withdrawn by suction, or vacuum, and passes through the probe 16, wherein a portion thereof, consisting essentially of air and steam, is withdrawn, again by suction, by line 20 wherein it is passed to any suitable, or conventional, oxygen analyzer 22 for analysis of its oxygen content. The remainder of the stream passing through probe 16, that is, the rest of the air, steam, water and pulverized coal is also removed by suction through the exit end of probe 16 by line 24 to any suitable collection unit.

Figure 2:
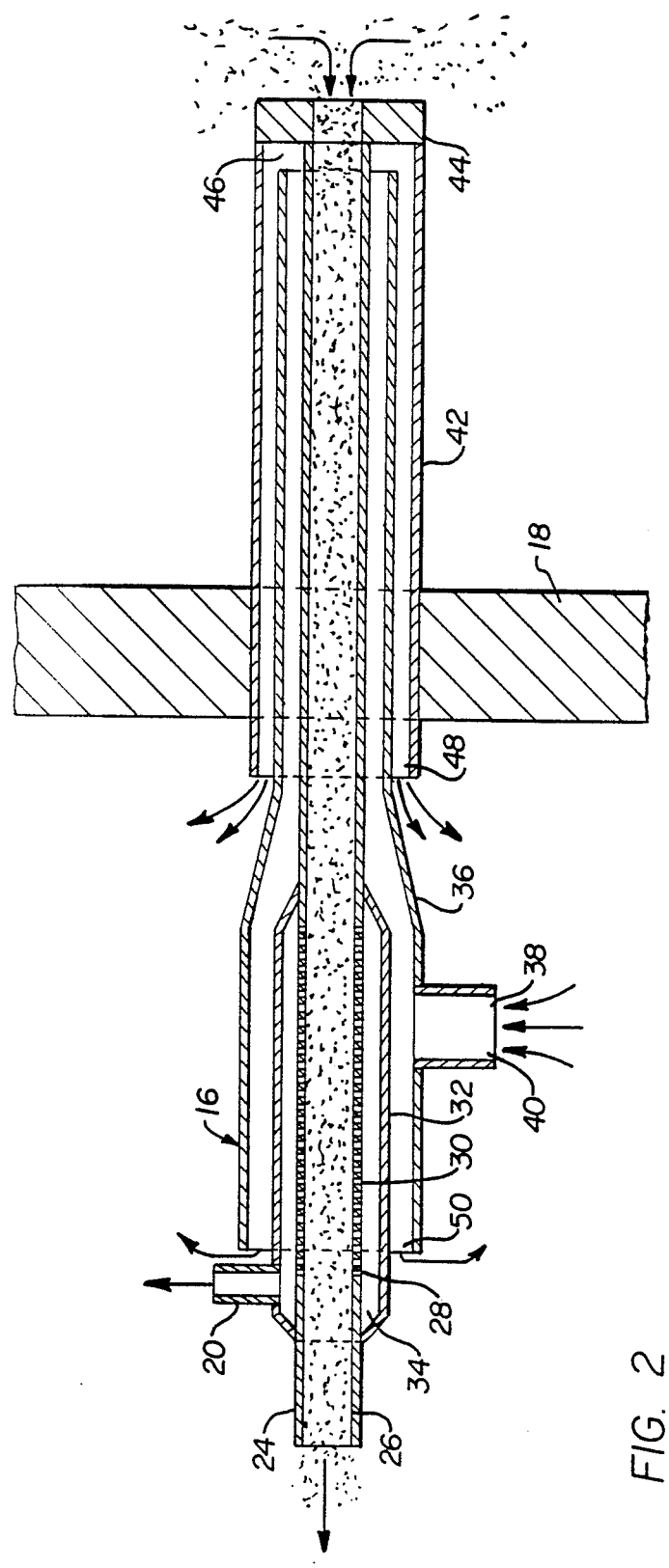
FIG. 2 is a cross-section of our novel claimed apparatus.

The novel apparatus, or probe, that we employ to carry out the claimed process herein is illustrated in greater detail in FIG. 2. As seen, the probe 16 comprises a first elongated tubular member 26 which extends through the wall 18 of coal pulverizer 2 and into the interior thereof for withdrawing therefrom a sample of the contents therein. During the inerting operation, when steam is introduced by line 14 into the interior of coal pulverizer 2, the contents therein will comprise coal particles, air, water and steam. The first elongated tubular member 26 is provided with a section 28 having passages 30 extending through the wall thereof. Axially surrounding section 28 of first elongated tubular member 26 is a second elongated tubular member 32 securedly attached thereto, by any means and forming an elongated chamber 34 therewith. Tubular member 32, is provided with a discharge line 20, also shown in FIG. 1, for withdrawing the gaseous content in said elongated chamber 34 and passing the same to oxygen analyzer 22.

In order to maintain the temperature of the stream flowing through elongated tubular member 26 within the range required to obtain the desired results herein, the walls of elongated tubular member 26 and of elongated chamber 34 are heated by any suitable means, for example, electrically by winding suitable wires carrying an electrical current therearound. In the preferred embodiment, however, illustrated in FIG. 2, such heating is obtained by contacting the outer walls of elongated tubular member 26 and elongated chamber 34 with a heated fluid, such as air or water. This is preferably done by axially disposing around at least a portion of said first elongated tubular member 26 and said elongated chamber 34 a third elongated tubular member 36 provided with an inlet line 38 for introduction therein of a heated fluid 40. In this way the heated fluid comes in contact with the outer surfaces of elongated tubular member 26 and elongated chamber 34 to heat the same and therefore the stream flowing therethrough. In order to avoid intermixing of the hot fluid 40 with the contents of coal pulverizer 2, which obviously would tend to dilute said contents and result in an inaccurate reading of the sample in line 20, a fourth elongated tubular member 42 is axially disposed around that portion of third elongated tubular member 36 that extends into the interior of coal pulverizer 2 and around at least a portion of said third elongated tubular member 36 externally of the wall 18 of coal pulverizer 2. In addition, the end of elongated tubular member 26 within coal pulverizer 2 is sealed, by any suitable means, for example, a cap 44, to the adjacent end of the fourth elongated tubular member 42, and suitable means 46 is provided for communication between the interior of third elongated tubular member 36 and the interior of fourth tubular member 42. In lieu of communicating means 46, or in addition to said communicating means 46, communicating means can also be provided, such as openings in the wall of third elongated tubular member 36 adjacent to said fourth elongated tubular member 42. Thus, the hot fluid entering inlet line 38 can flow laterally in the space between elongated tubular member 26 and elongated chamber 34 and third elongated tubular member 36, pass through communicating means 46, reverse its flow through the space between third elongated tubular member 36 and fourth elongated tubular member 42 and then be discharged from exit 48 external of coal pulverizer 2 TM Additional hot fluid can also be discharged external of coal pulverizer 2 from exit 50.

In order to obtain the desired effect herein, the passages 30 in section 28 of first elongated tubular member 26 must be small enough to prevent the flow therethrough of all, or substantially all, of the coal particles in the stream passing through first elongated tubular member 26. The diameter of the passages 30 must not exceed about 25 microns. In order to prevent, or substantially inhibit, deposition of the coal particles in the stream passing through tubular member 26 on the inner walls thereof or in the passages 30, it is necessary that the velocity of the stream be maintained in the range of about 20 to about 120 feet per second. To prevent, or substantially inhibit, condensation of steam in the stream passing through first tubular member 26, which would tend to obstruct flow of said stream therethrough and adversely affect the analyses of the sample in oxygen analyzer 22, it is critical to maintain the temperature of the stream in first elongated tubular member 26 and elongated chamber 34 within the range of about 1° to about 10° F. above the temperature in the coal pulverizer 2. Sufficient hot fluid is introduced into the system to maintain the stream in the probe 16 within the above range. In order to continuously draw a stream out of the local pulverizer 2 and to discharge the stream from probe 16, a vacuum on the order of about 0.5 to about 6.0 inches of water column is sufficient. A vacuum in the range of about 1.0 to about 7.0 inches of water column is sufficient to withdraw a sample of the stream from first elongated tubular member 26 and to pass the same to oxygen analyzer 22 by means of line 20.

By operating the process as defined herein, the temperature of the sample removed from the pulverizer remains consistent with the temperature of the system within the pulverizer, the partial pressure of the steam through the sampling procedure remains unaffected, no moisture forms on the wall of the probe, no particles deposit on the wall of the probe nor in the passageways therein and the sample obtained is an accurate representation of the contents of the pulverizer.

EXAMPLE

A stream was withdrawn from a pulverizer containing 20 weight percent of coal having a particle size of 20 to 300 microns, 35 weight percent of water, 50 volume percent of air and 50 volume percent of steam at a temperature of 150° F. and a vacuum of 2 inches of water column and was passed through a tube having an internal diameter of 0.555 inch at a velocity of 50 feet per second and was heated to a temperature of about 152° F. Through a portion of the tube having passages in the wall thereof having average diameter of 10 microns, a mixture of air and steam was withdrawn therefrom using a vacuum of 3 inches of water column and was analyzed for its oxygen content. The remainder of the stream was withdrawn from the tube an discharged from the system. The volume ratio of steam to air sent to the oxygen analyzer was found to be consistent with the volume ratio of steam to air in the pulverizer.

Obviously, many modifications and variations of the invention as hereinabove set forth can be made herein without departing from the spirit and scope of thereof, and therefore only such limitations should be made as are indicated in the appended claims.

We claim:

1. A probe capable of obtaining a gaseous sample from a stream containing solid particulate material, a gas, water, and steam which comprises a first elongated tubular member, wherein said stream is capable of entering therein at one end thereof and capable of being discharged at the other end thereof, provided with a section having passages extending through the wall thereof, a second elongated tubular member axially surrounding said section of said first tubular member having said passages extending through-the-wall thereof, said second elongated tubular member forming a closed elongated chamber with said first elongated tubular member, a discharge tube extending outwardly from said elongated chamber and means for heating the walls of said first and said second elongated tubular members.

2. The probe of claim 1 wherein said heating means comprises a third elongated tubular member axially disposed around said first and second elongated tubular members and means extending through the wall of said third elongated tubular member for introducing a heated fluid therein.

3. The probe in claim 3 wherein a fourth elongated tubular member is axially disposed around at least a portion of said third elongated tubular member, said first elongated tubular member at said one end thereof being sealed to the adjacent end of said fourth elongated tubular member and means for communicating the interior of said third elongated tubular member with the adjacent interior of said fourth elongated tubular member.

4. A process for obtaining a gaseous sample from a stream containing solid particulate material, a gas, water and steam which comprises withdrawing a stream containing said particulate material, a gas, water and steam from a system containing the same through an elongated tubular member extending into said system and discharging said stream from said tubular member externally of said system, heating said stream in its passage through said tube and removing from said tubular member externally of said system a gaseous sample consisting essentially of said gas and said steam through a porous section of said elongated tubular member having openings in the wall thereof smaller in cross-section than the solid particulate material in said stream, said stream being passed through said elongated tubular member at a velocity such that deposition of said particulate material on the inner walls thereof is substantially inhibited.

5. The process of claim 4 wherein said particulate material is coal and said gas is air.

6. The process of claim 4 wherein said stream is heated to a temperature of within the range of about 1° to about 10° F. above the temperature in said system.

7. The process of claim 4 wherein said porous section has openings not exceeding about 25 microns.

8. The process of claim 4 wherein said system is a coal pulverizer, said particulate material is coal and said gas is air, said stream is heated a temperature within the range of about of about 1° to about 10° F. above the temperature in said system, said porous section has openings having diameters not exceeding about 25 microns, said heating is obtained by indirect contact with a hot fluid and said hot fluid is maintained out of contact with the contents of said system.

9. The process of claim 4 wherein said heating is obtained by indirect contact with a hot fluid.

10. The process of claim 9 wherein said fluid is hot air.

11. The process of claim 9 wherein said hot fluid is maintained out of contact with the contents of said system.

* * * * *